US00PP29007P2

(12) United States Plant Patent
Uchneat

(10) Patent No.: US PP29,007 P2
(45) Date of Patent: Feb. 27, 2018

(54) ***LAGERSTROEMIA* PLANT NAMED 'G2X133181'**

(50) Latin Name: *Lagerstroemia indica*
Varietal Denomination: G2X133181

(71) Applicant: Michael Uchneat, Bellefonte, PA (US)

(72) Inventor: Michael Uchneat, Bellefonte, PA (US)

(73) Assignee: Garden Genetics, LLC, Bellefonte, PA (US)

( * ) Notice: Subject to any disclaimer, the term of this patent is extended or adjusted under 35 U.S.C. 154(b) by 0 days.

(21) Appl. No.: 15/330,710

(22) Filed: Oct. 27, 2016

(51) Int. Cl.
*A01H 5/02* (2006.01)

(52) U.S. Cl.
USPC ..... Plt./252

(58) Field of Classification Search
USPC ..... Plt./226, 252
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Lagerstroemia* cultivar named 'G2X133181' is disclosed, characterized by rose-magenta blooms on a plant with red stems and dark green leaves. Plants have an attractive upright and arching growth habit, good basal branching and grow proportionately wide as tall. The new variety is a *Lagerstroemia*, normally used for outdoor ornamental purposes.

2 Drawing Sheets

Latin name of the genus and species: *Lagerstroemia indica.*

Variety denomination: 'G2X133181'.

BACKGROUND OF THE INVENTION

The new *Lagerstroemia* cultivar is a product of a planned breeding program conducted by the inventor, Michael Uchneat, in Bellefonte, Pa. The objective of the breeding program was to produce new *Lagerstroemia* varieties with a compact habit, superior winter hardiness and dense flowering. The open pollination resulting in this new variety was made during August of 2010.

The seed parent is the, patented commercial variety referred to as *Lagerstroemia* 'Red Filli' U.S. Plant Pat. No. 14,353. The pollen parent is unknown as it was an open pollination breeding program. The new variety was selected September of 2011 by the inventor in a group of seedlings resulting from the 2010 open pollination, in a seedling trial field in Bellefonte, Pa.

Asexual reproduction of the new cultivar was performed by softwood cuttings. This was first performed at Spring Meadow Nursery in Bellefonte, Pa. during February of 2012 and has shown that the unique features of this cultivar are stable and reproduced true to type in multiple successive generations.

SUMMARY OF THE INVENTION

The cultivar 'G2X133181' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G2X133181' These characteristics in combination distinguish 'G2X133181' as a new and distinct *Lagerstroemia* cultivar:

1. Rose magenta flower color
2. Red stems with dark green leaves
3. Upright arching growth habit.
4. Plants are as wide as they are tall.
5. Good basal branching.

Plants of the new cultivar 'G2X133181' are similar to plants of the seed parent, *Lagerstroemia* in most horticultural characteristics, however, plants of the new cultivar 'G2X133181' differ in the following;

1. The new variety has a magenta rose colored flower, the seed parent has red flowers.
2. The new variety forms a dense plant from basal branching, the seed parent has loose branching.

COMMERCIAL COMPARISON

Plants of the new cultivar 'G2X133181' are comparable to the commercial variety *Lagerstroemia* 'Infiniti Brite Pink', unpatented. The two *Lagerstroemia* varieties are similar in most horticultural characteristics; however, the new variety 'G2X133181' differs in the following:

1. The new variety has a darker pink flower.

BRIEF DESCRIPTION OF THE PHOTOGRAPHS

Figure 1:
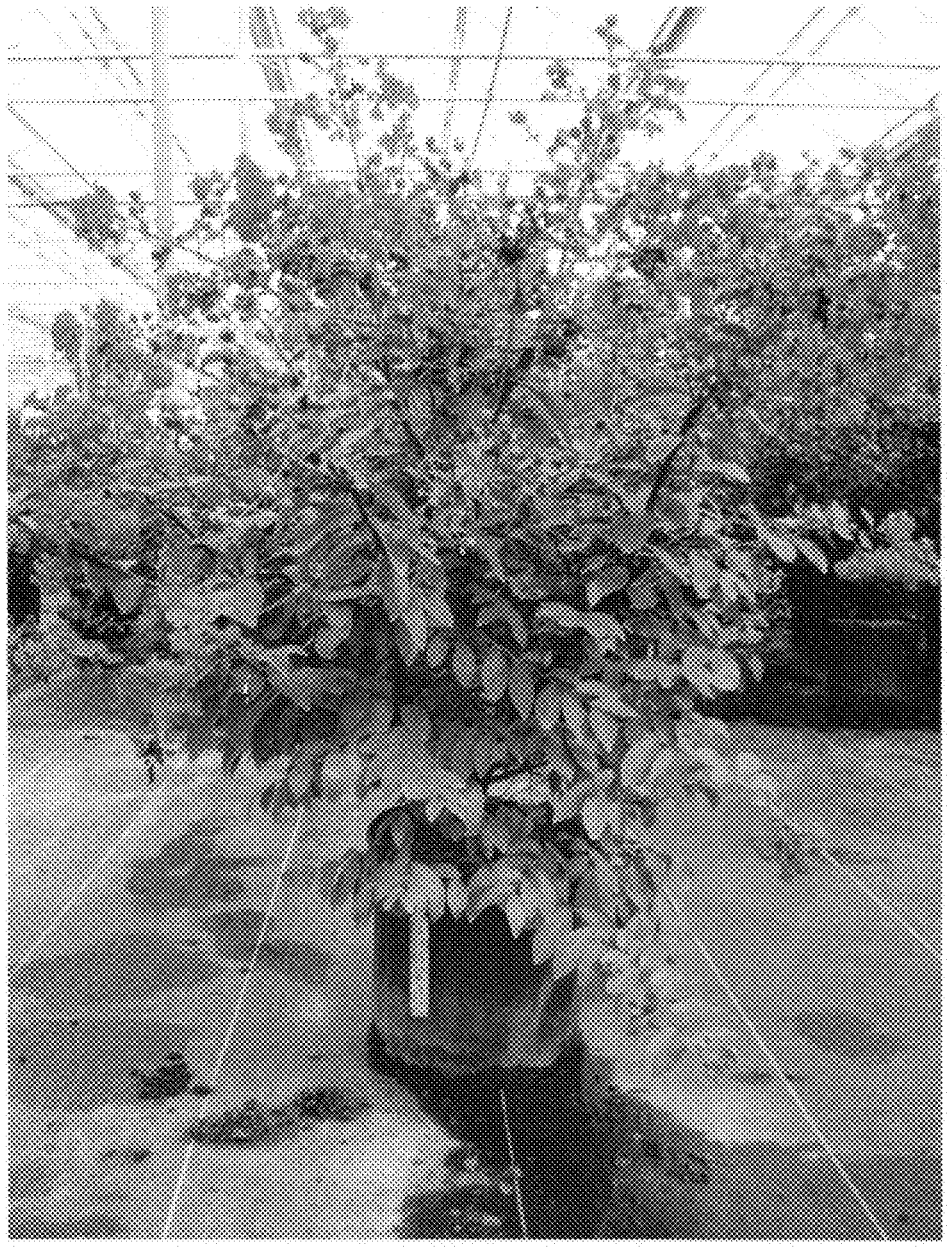

The accompanying photograph in FIG. 1 illustrates in full color a typical plant of 'G2X133181' grown in a poly hoop house in Bellefonte, Pa. Age of the plant photographed is approximately 2 years old from a rooted cutting.

Figure 2:
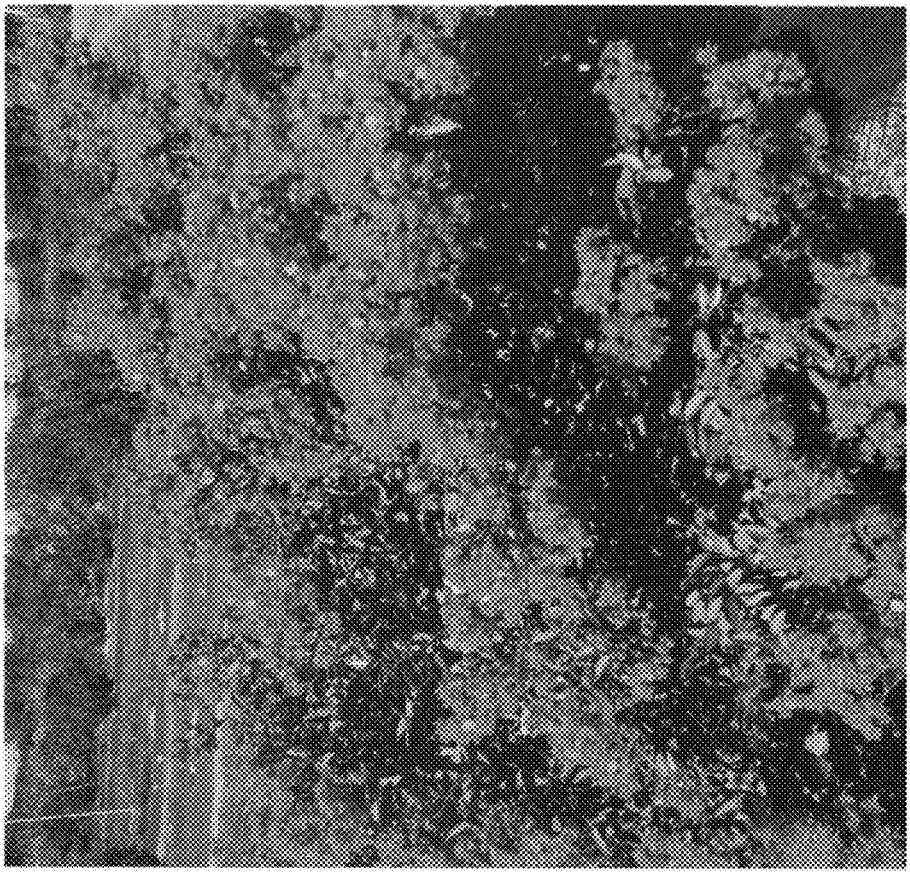

FIG. 2 illustrates a more mature plant of approximately 3 years, growing in the ground.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'G2X133181' plants grown in a poly house during April of 2016 in Bellefonte, Pa. The growing temperature ranged from approximately 18° C. to 27° C. during the day and from approximately 5° C. to 10° C. during the night. General light conditions are normal sunlight and numerical values represent averages of typical plant types.

Botanical classification: *Lagerstroemia indica* 'G2X133181'.

PROPAGATION

Type of propagation typically used: Terminal vegetative cutting.

Time to initiate roots: About 14-21 days at about 24° C.

Time to produce a rooted cutting: About 28-35 days at about 24° C.

Root description: Thin fibrous, not fleshy, freely branching. White in color, not accurately measured with R.H.S. Chart.

PLANT

Age of plant described: 2-3 years old from a rooted cutting.
Container size: 3 gallon container.
Overall plant shape: Upright, rounded.
Growth habit: Freely branching outward.
Plant spread: 90 cm.
Plant height: 90 cm.
Growth rate: Fast.
Plant vigor: Good.
Branching habit: Basal, some pinching required.
Length of primary lateral branches: Average range 25 to 35 cm.
Diameter of lateral branches: 0.4 cm.
Quantity of lateral branches: 30.
Stem:
- *Color*.—New growth upper section near Greyed-Red 181A. Lower section near Yellow-Green 148A. Bark colored near Grey-Brown 199A.
- *Shape*.—Square shaped stem.
- *Strength*.—Strong.
- *Aspect angle*.—45°.
- *Texture*.—Pubescent, then woody with age.

Internode length: 3.0 to 3.5 cm.

FOLIAGE

Leaf:
- *Arrangement*.—Sub-opposite, single.
- *Average length*.—4.0 to 5.5 cm.
- *Average width*.—2.0 to 2.5 cm.
- *Shape of blade*.—Lanceolate-elliptical.
- *Apex*.—Acute.
- *Base*.—Rounded.
- *Margin*.—Entire.
- *Texture of top surface*.—Smooth, slightly pubescent around margin and center vein.
- *Texture of bottom surface*.—Smooth, waxy.
- *Color*.—Young foliage upper side: Near RHS Greyed-purple 183A. Young foliage under side: Near RHS Greyed-purple 183A. Mature foliage upper side: Near RHS Green 141B. Mature foliage under side: Near RHS Green 143A.
- *Venation*.—Type: Pinnate. Venation color upper side: Near RHS Green 143A. Venation color under side: Near RHS Green 143A.
- *Petiole*.—Leaves sessile.

FLOWER

Natural flowering season: June through October.
Inflorescence form: Panicles.
Flowers per inflorescence: Smaller panicles: average 15. Larger panicles average 60.
Inflorescence size:
- *Larger, mature panicles*.—Width: 31.5 cm. Height: 32.25 cm.
- *Smaller, lower occuring panicles*.—Width: 10.5 cm. Height: 32.25 cm.

Individual flowers:
- *Type*.—Rotate.
- *Shape*.—Whorl of 6 freely attached petals.
- *Habit*.—Outward facing.
- *Diameter*.—4.0 cm.
- *Length*.—4.0 cm.
- *Depth*.—1.5 cm.
- *Persistence*.—Self-cleaning.
- *Fragrance*.—Subtle floral scent.

Petals:
- *Arrangement*.—Whorled, not fused.
- *Number*.—6.
- *Shape*.—Orbicular.
- *Margin*.—Irregular undulate.
- *Tip shape*.—Rounded.
- *Base shape*.—Rounded.
- *Length*.—Average 1.2 cm.
- *Width*.—Average 1.2 cm.
- *Texture*.—Upper: Soft, smooth, delicate papery. Lower: Soft, smooth, delicate papery.
- *Color*.—When opening: Upper surface: Near RHS Red-Purple 67A. Under surface: Near RHS Red-Purple 67A. Fully opened: Upper surface: Near RHS Red-Purple 67A. Under surface: Near RHS Red-Purple 67A. Fading: Upper surface: Near RHS Red-Purple 67A. Under surface: Near RHS Red-Purple 67A.

Bud:
- *Shape*.—Obovate.
- *Length*.—9.0 mm.
- *Diameter*.—7. mm.
- *Color*.—Near RHS Red-purple 60A.

Sepals:
- *Appearance*.—Matte.
- *Arrangement*.—Unguiculate.
- *Shape*.—Narrowly triangular.
- *Tip shape*.—Acute.
- *Base shape*.—Obtuse.
- *Margin*.—Entire.
- *Quantity per flower*.—6.
- *Length*.—2.8 mm.
- *Width*.—4 mm.
- *Margin*.—Entire.

*Texture*.—Upper: Smooth, coriaceous, rugose. Lower: Smooth.

*Color*.—Upper: Near RHS Greyed-green 190B. Lower: Near RHS Red-purple 60A.

Calyx:

*Shape*.—Unguiculate.

*Length*.—5 mm.

*Diameter*.—5 mm.

Peduncle:

*Length*.—4 to 10 cm.

*Diameter*.—About 4 mm.

*Texture*.—Smooth.

*Color*.—Near RHS Red-purple 60A.

*Orientation*.—Upright and outward.

*Strength*.—Good.

Pedicel:

*Length*.—15 mm.

*Diameter*.—0.5 mm.

*Angle*.—Outwardly facing.

*Strength*.—Good.

*Texture*.—Smooth.

*Color*.—Near RHS Red-purple 60A.

REPRODUCTIVE ORGANS

Stamens:

*Number*.—*About* 29.

*Filament length*.—0.8-1.2 cm.

*Filament color*.—Outer filaments near 60A, inner filaments near White 155A.

Anthers:

*Shape*.—Linear.

*Length*.—1 mm.

*Color*.—Near RHS Yellow-orange 15B.

*Pollen*.—Not observed.

Pistil:

*Number*.—1.

*Length*.—2.0 cm.

*Style*.—Length: 2.0 cm. Color: Near RHS Red-Purple 60A.

*Stigma*.—Shape: Globular. Color: Near RHS Black 200A. Ovary color: Near RHS Yellow 4A.

OTHER CHARACTERISTICS

Fruits and seeds: Not observed to date.

Disease/pest resistance: Neither resistance nor susceptibility to normal diseases of *Lagerstroemia*.

Temperature range: Observed to tolerate a temperature range from −28° C. to 35° C. At the lowest temperature, −28° C., plant may die back, but, roots will survive, allowing plant to grow back.

What is claimed is:

1. A new and distinct cultivar of *Lagerstroemia* plant named 'G2X133181' as herein illustrated and described.

* * * * *